United States Patent [19]

Bagli et al.

[11] 4,066,784

[45] Jan. 3, 1978

[54] TROPONE DERIVATIVES

[75] Inventors: Jehan F. Bagli, Kirkland; Tibor Bogri, Montreal, both of Canada

[73] Assignee: Ayerst, McKenna and Harrison Ltd., Montreal, Canada

[21] Appl. No.: 697,295

[22] Filed: June 17, 1976

[51] Int. Cl.$^2$ .................. C07C 153/09; C07C 103/32; C07C 55/06; A61K 31/215

[52] U.S. Cl. ............................... 424/305; 260/455 R; 260/514 J; 260/514 K; 260/518 R; 260/519; 260/520 R; 260/520 C; 424/301; 424/308; 424/309; 424/317; 560/43; 560/51; 560/53; 560/125; 560/126

[58] Field of Search ............. 260/468 J, 514 J, 471 A, 260/518 R, 519; 424/305, 309, 317

[56] References Cited

PUBLICATIONS

Sellstedt et al., J. Med. Chem. 18 926, (1975).

*Primary Examiner*—Robert Gerstl
*Attorney, Agent, or Firm*—Stephen Venetianer

[57] ABSTRACT

Tropone derivatives substituted with an amino-derivative of oxalic acid or acetic acid are disclosed. In addition, the tropone nucleus can be optionally further substituted. The foregoing compounds are useful for preventing or treating allergic conditions in a mammal. Methods for the preparation and use of the compounds are disclosed.

6 Claims, No Drawings

TROPONE DERIVATIVES

BACKGROUND OF THE INVENTION a. Field of the Invention

This invention relates to novel tropone derivatives, to processes for their preparation, to methods for using said derivatives, and to therapeutically acceptable salts and compositions of said derivatives.

More specifically, the present invention relates to novel tropone derivatives possessing valuable pharmacologic properties. For example, these derivatives are useful for preventing or treating allergic conditions in a mammal at dosages which do not elicit undesirable side effects. The combination of these pharmacologic properties renders the tropone derivatives of the invention therapeutically useful.

b. Description of the Prior Art

A rather large number of reports dealing with tropone derivatives are available. The prior art relating to tropones is summarized in various reviews; for example, see the review by F. Pietra in Chem. Rev., 73, 293 (1973). In addition, other tropone derivatives are reported; for instance, a class of alkyl esters of 5-amidotropoles is described by L. D. Donaruma, Canadian Pat. No. 787,451, issued June 11, 1968; N-troponyl amino acid esters are described in the Japanese Pat. No. 24371/63, issued Nov. 15, 1963; and (2-troponylthio)acetic acid is described by T. Nozoe et. al., Proc. Japan Acad., 29, 22 (1953).

The tropone derivatives of the present invention are distinguished from the prior art compounds by the nature of the substituents on the tropone nucleus and by their pharmacologic properties.

SUMMARY OF THE INVENTION

The compounds of this invention are represented by formula I

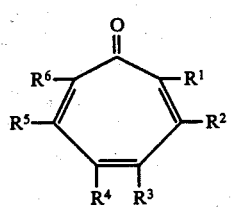

(1)

in which $R^1$, $R^2$, $R^3$, $R^4$, $R^5$ and $R^6$ are the same or different selected from the group consisting of hydrogen; halo; trifluoromethyl; lower alkoxy; lower alkyl; phenyl; hydroxy; phenoxy; mercapto; $NR^7R^8$ wherein each of $R^7$ and $R^8$ is hydrogen or lower alkyl; and a radical of formula $Y$-$CR^9R^{10}$-$COOR^{11}$ wherein Y is O, S or $NR^{12}$ wherein $R^{12}$ is hydrogen or lower alkyl, $R^9$ and $R^{10}$ together are oxo and $R^{11}$ is hydrogen or lower alkyl, or Y is SO or $SO_2$, $R^9$ and $R^{10}$ are hydrogen and $R^{11}$ is hydrogen or lower alkyl; with the proviso that one, two or three of $R^1$, $R^2$, $R^3$, $R^4$, $R^5$, $R^6$ must be a radical of formula $Y$-$CR^9R^{10}$-$COOR^{11}$ wherein, Y, $R^9$, $R^{10}$ and $R^{11}$ are as defined in each instance herein; and with the additional proviso that when $R^1$ and/or $R^4$ is a radical of formula $Y$-$CR^9R^{10}$-$COOR^{11}$ wherein Y is $NR^{12}$ wherein $R^{12}$ is as defined herein, $R^9$ and $R^{10}$ together are oxo and $R^{11}$ is as defined herein, then at least one of $R^2$, $R^3$, $R^5$ and $R^6$ must be a radical of formula $Y$-$CR^9R^{10}$-$COOR^{11}$ wherein Y, $R^9$, $R^{10}$ and $R^{11}$ are as defined in each instance herein.

A preferred group of compounds of this invention is represented by formula I in which $R^1$, $R^2$, $R^3$, $R^4$, $R^5$ and $R^6$ are the same or different selected from the group consisting of hydrogen or a radical of formula $Y$-$CR^9R^{10}$-$COOR^{11}$ wherein Y is O, S or $NR^{12}$ wherein $R^{12}$ is hydrogen or lower alkyl, $R^9$ and $R^{10}$ together are oxo and $R^{11}$ is hydrogen or lower alkyl, or Y is SO or $SO_2$, $R^9$ and $R^{10}$ are hydrogen and $R^{11}$ is hydrogen or lower alkyl; with the proviso that one, two or three of $R^1$, $R^2$, $R^3$, $R^4$, $R^5$ and $R^6$ must be a radical of formula $Y$-$CR^9R^{10}$-$COOR^{11}$ wherein Y, $R^9$, $R^{10}$ and $R^{11}$ are as defined in each instance herein; and with the additional proviso that when $R^1$ and/or $R^4$ is a radical of formula $Y$-$CR^9R^{10}$-$COOR^{11}$ wherein Y is $NR^{12}$ wherein $R^{12}$ is as defined herein, $R^9$ and $R^{10}$ together are oxo and $R^{11}$ is as defined herein, then at least one of $R^2$, $R^3$, $R^5$ and $R^6$ must be a radical of formula $Y$-$CR^9R^{10}$-$COOR^{11}$ wherein Y, $R^9$, $R^{10}$ and $R^{11}$ are as defined in each instance herein.

Another preferred group of compounds of this invention is represented by formula I in which a. $R^1$ is a radical of formula $Y$-$CR^9R^{10}$-$COOR^{11}$ wherein Y is O or S, $R^9$ and $R^{10}$ together are oxo and $R^{11}$ is hydrogen or lower alkyl, and $R^2$, $R^3$, $R^4$, $R^5$ and $R^6$ are hydrogen; or b. $R^1$ is a radical of formula $Y$-$CR^9R^{10}$-$COOR^{11}$ wherein Y is SO or $SO_2$, $R^9$ and $R^{10}$ are hydrogen and $R^{11}$ is hydrogen or lower alkyl, and $R^2$, $R^3$, $R^4$, $R^5$ and $R^6$ are hydrogen; or c. each of $R^1$ and $R^6$ is a radical of formula $Y$-$CR^9R^{10}$-$COOR^{11}$ wherein Y is $NR^{12}$ wherein $R^{12}$ is hydrogen or lower alkyl, $R^9$ and $R^{10}$ together are oxo and $R^{11}$ is hydrogen or lower alkyl, and $R^2$, $R^3$, $R^4$ and $R^5$ are hydrogen.

The therapeutically acceptable salts of the compounds of formula I are also included within the scope of this invention.

The compounds of this invention of formula I are prepared by a process comprising:

condensing a compound of formula II

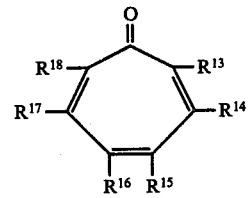

(II)

in which $R^{13}$, $R^{14}$, $R^{15}$, $R^{16}$, $R^{17}$ and $R^{18}$ are the same or different selected from the group consisting of hydrogen; halo; trifluoromethyl; lower alkoxy; lower alkyl; phenyl; hydroxy; phenoxy; mercapto; $NR^7R^8$ wherein $R^7$ is lower alkyl and $R^8$ is hydrogen or lower alkyl; and $NHR^{12}$ wherein $R^{12}$ is hydrogen or lower alkyl; with the proviso that one, two or three of $R^{13}$, $R^{14}$, $R^{15}$, $R^{16}$, $R^{17}$ and $R^{18}$ must be hydroxy, mercapto or $NHR^{12}$ wherein $R^{12}$ is as defined herein, and with the additional proviso that when $R^{13}$ and/or $R^{16}$ is $NHR^{12}$, then at least one of $R^{14}$, $R^{15}$, $R^{17}$ and $R^{18}$ must be $NHR^{12}$, hydroxy or mercapto with a compound of formula III Halogen-$CR^9R^{10}$-$COOR^{11}$ (III)

in which $R^9$ and $R^{10}$ are as defined herein, $R^{11}$ is lower alkyl and the halogen is bromine, chlorine or iodine in the presence of a proton acceptor to obtain the corresponding compound of formula I in which $R^1$, $R^2$, $R^3$, $R^4$, $R^5$ and $R^6$ are the same or different selected from the group consisting of hydrogen; halo; trifluoromethyl; lower alkoxy; lower alkyl; phenyl; hydroxy; phenoxy; $NR^7R^8$ is lower alkyl and $R^8$ is hydrogen or lower alkyl; and a radical of formula $Y$-$CR^9R^{10}$-$COOR^{11}$ wherein Y is O, S or $NR^{12}$ wherein $R^{12}$ is as defined herein, $R^9$ and $R^{10}$ together are oxo and $R^{11}$ is lower alkyl, with the proviso that when $R^1$ and/or $R^4$ is a radical of formula $Y$-$CR^9R^{10}$-$COOR^{11}$ wherein Y is $NR^{12}$, $R^9$ and $R^{10}$ together are oxo and $R^{11}$ is lower alkyl, then at least one of $R^2$, $R^3$, $R^5$ and $R^6$ must be a radical of formula $Y$-$CR^9R^{10}$-$COOR^{11}$ wherein Y is O, S or $NR^{12}$, $R^9$ and $R^{10}$ together are oxo and $R^{11}$ is lower alkyl; and the corresponding intermediate of formula IV

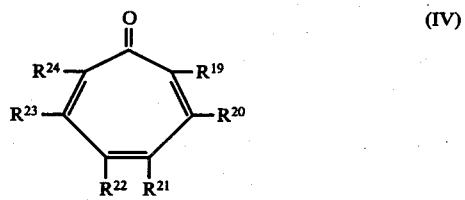

in which $R^{19}$, $R^{20}$, $R^{21}$, $R^{22}$, $R^{23}$ and $R^{24}$ are the same or different selected from the group consisting of hydrogen; halo; trifluoromethyl; lower alkoxy; lower alkyl; phenyl; hydroxy; phenoxy; $NR^7R^8$ wherein $R^7$ is lower alkyl and $R^8$ is hydrogen or lower alkyl; and a radical of formula $Y$-$CR^9R^{10}$-$COOR^{11}$ wherein Y is S, $R^9$ and $R^{10}$ are hydrogen and $R^{11}$ is lower alkyl, and oxidizing the intermediate of formula IV to obtain the corresponding compound of formula I in which $R^1$, $R^2$, $R^3$, $R^4$, $R^5$ and $R^6$ are the same or different selected from the group consisting of hydrogen; halo; trifluoromethyl; lower alkoxy; lower alkyl; phenyl; hydroxy; phenoxy; $NR^7R^8$ wherein $R^7$ is lower alkyl and $R^8$ is hydrogen or lower alkyl; and a radical of formula $Y$-$CR^9R^{10}$-$COOR^{11}$ wherein Y is SO or $SO_2$, $R^9$ and $R^{10}$ are hydrogen and $R^{11}$ is lower alkyl; and if desired and required, followed by transformation of the compound of formula I, prepared as described above, to other compounds of formula I by methods described herein.

In another embodiment of the process of this invention, the compound of formula II in which $R^{13}$, $R^{14}$, $R^{15}$, $R^{16}$, $R^{17}$ and $R^{18}$ are the same or different selected from the group consisting of hydrogen; halo; trifluoromethyl; lower alkoxy; lower alkyl; phenyl; phenoxy; $NR^7R^8$ wherein each of $R^7$ and $R^8$ is lower alkyl; with the proviso that at least one of $R^{13}$, $R^{14}$, $R^{15}$, $R^{16}$, $R^{17}$ and $R^{18}$ must be lower alkoxy or halo wherein the halo is selected from chlorine, bromine or iodine is condensed with a compound of formula V $$\text{H-Y-CR}^9\text{R}^{10}\text{-COOR}^{11} \qquad (V)$$

in which $R^9$ and $R^{10}$ are hydrogen, $R^{11}$ is lower alkyl and Y is S in the presence of a proton acceptor to obtain the corresponding intermediate of formula IV in which $R^{19}$, $R^{20}$, $R^{21}$, $R^{22}$, $R^{23}$ and $R^{24}$ are the same or different selected from the group consisting of hydrogen; trifluoromethyl; lower alkyl; phenyl; phenoxy; $NR^7R^8$ wherein each of $R^7$ and $R^8$ is lower alkyl and a radical of formula $Y$-$CR^9R^{10}$-$COOR^{11}$ wherein Y is S, $R^9$ and $R^{10}$ are hydrogen and $R^{11}$ is lower alkyl, with the proviso that at least one of $R^{19}$, $R^{20}$, $R^{21}$, $R^{22}$, $R^{23}$ or $R^{24}$ is the radical of formula $Y$-$CR^9R^{10}$-$COOR^{11}$ as defined in the last instance, and oxidizing the intermediate of formula IV to obtain the corresponding compound of formula I in which $R^1$, $R^2$, $R^3$, $R^4$, $R^5$ and $R^6$ are the same or different selected from the group consisting of hydrogen; trifluoromethyl; lower alkyl; phenyl; phenoxy; $NR^7R^8$ wherein each of $R^7$ and $R^8$ is lower alkyl; and a radical of formula $Y$-$CR^9R^{10}$-$COOR^{11}$ wherein Y is SO or $SO_2$, $R^9$ and $R^{10}$ are hydrogen and $R^{11}$ is lower alkyl; and, if desired and required, followed by transformation of the compound of formula I, prepared as described above, to other compounds of formula I by methods described herein.

More specifically, the transformation of the compound of formula I, prepared as described above, to other compounds of formula I comprises:

reacting the compound of formula I in which at least one of $R^1$, $R^2$, $R^3$, $R^4$, $R^5$ and $R^6$ is lower alkoxy, chlorine, bromine or iodine with ammonia or an amine of formula $HNR^7R^8$ wherein each of $R^7$ and $R^8$ is hydrogen or lower alkyl to obtain the corresponding compound of formula I in which the corresponding $R^1$, $R^2$, $R^3$, $R^4$, $R^5$ and $R^6$ is $NR^7R^8$ wherein each of $R^7$ and $R^8$ is hydrogen or lower alkyl;

reacting the compound of formula I in which at least one of $R^1$, $R^2$, $R^3$, $R^4$, $R^5$ and $R^6$ is lower alkoxy, chlorine, bormine or iodine with sodium sulfhydrate to obtain the corresponding compound of formula I in which the corresponding $R^1$, $R^2$, $R^3$, $R^4$, $R^5$ and $R^6$ is mercapto; and hydrolyzing the compound of formula I, prepared as described above, in which at least one of $R^1$, $R^2$, $R^3$, $R^4$, $R^5$ and $R^6$ is a radical of formula $Y$-$CR^9R^{10}$-$COOR^{11}$ wherein $R^9$, $R^{10}$ and Y are as defined in each instance herein and $R^{11}$ is lower alkyl to obtain the corresponding compound of formula I in which the corresponding $R^1$, $R^2$, $R^3$, $R^4$, $R^5$ and $R^6$ is a radical of formula $Y$-$CR^9R^{10}$-$COOR^{11}$ wherein $R^9$, $R^{10}$ and Y are as defined herein and $R^{11}$ is hydrogen.

Another aspect of this invention involves a method for preventing or treating allergic conditions in a mammal which comprises administering to said mammal an allergy alleviating effective amount of a compound of formula I, or a therapeutically acceptable salt thereof.

Still another aspect involves a pharmaceutical composition comprising a compound of formula I, or a therapeutically acceptable salt thereof, and a pharmaceutically acceptable carrier.

DETAILED DESCRIPTION OF THE INVENTION

The term "lower alkyl" as used herein contemplates both straight and branched chain alkyl radicals containing from one to six carbon atoms and includes methyl, ethyl, propyl, isopropyl, butyl, isobutyl, pentyl, hexyl and the like.

The term "lower alkoxy" as used herein contemplates both straight and branched chain alkoxy radicals containing from one to six carbon atoms and includes methoxy, ethoxy, isopropoxy, butoxy, hexanoxy and the like.

The term "halo" as used herein contemplates halogens and include fluorine, chlorine, bromine and iodine, unless stated otherwise.

The term "lower alkanol" as used herein contemplates both straight and branched chain alkanols containing from one to six carbon atoms and includes methanol, ethanol, isopropanol, butanol, hexanol and the like.

The acidic compounds of formula I in which $R^1$, $R^2$, $R^3$, $R^4$, $R^5$ and/or $R^6$ is a radical of formula $Y-CR^9R^{10}-COOR^{11}$ wherein Y, $R^9$ and $R^{10}$ are as defined herein and $R^{11}$ is hydrogen form salts with suitable therapeutically acceptable inorganic and organic bases. These derived salts possess the same activity as the parent acid and are included within the scope of this invention. The acid is transformed in excellent yield into the corresponding therapeutically acceptable salts by neutralization of said acid with the appropriate inorganic or organic base. The salts are administered in the same manner as the parent acid compounds. Suitable inorganic bases to form these salts include, for example, the hydroxides, carbonates, bicarbonates or alkoxides of the alkali metals or alkaline earth metals, for example, sodium, potassium, magnesium, calcium and the like. Suitable organic bases include the following amines; lower mono-, di- and trialkylamines, the alkyl radicals of which contain up to three carbon atoms, such as methylamine, dimethylamine, trimethylamine, ethylamine, di- and triethylamine, methylethylamine, and the like; mono-, di and trialkanolamines, the alkanol radicals of which contain up to three carbon atoms, for example, mono-, di and triethanolamine; alkylene-diamines which contain up to six carbon atoms, such as hexamethylenediamine; cyclic saturated or unsaturated bases containing up to six carbon atoms, such as pyrrolidine, piperidine, morpholine, piperazine and their N-alkyl and N-hydroxyalkyl derivatives, such as N-methyl-morpholine and N-(2-hydroxyethyl)-piperidine, as well as pyridine. Furthermore, there may be mentioned the corresponding quaternary salts, such as the tetraalkyl (for example tetramethyl), alkyl-alkanol (for example methyltrimethanol and trimethyl-monoethanol) and cyclic ammonium salts, for example the N-methylpyridinium, N-methyl-N-(2-hydroxyethyl)morpholinium, N,N-dimethylmorpholinium, N-methyl-N-(2-hydroxyethyl)morpholinium, N,N-dimethylpiperidinium salts, which are characterized by having good water-solubility. In principle, however, there can be used all the ammonium salts which are physiologically compatible.

The transformations to the salts can be carried out by a variety of methods known in the art. For example, in the case of the inorganic salts, it is preferred to dissolve the acid of formula I in water containing at least one equivalent amount of a hydroxide, carbonate, or bicarbonate corresponding to the inorganic salt desired. Advantageously, the reaction is performed in a water-miscible, inert organic solvent, for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent or a more moderate polarity, for example, a lower alkanol, for instance, butanol, or a lower alkanone, for instance, ethyl methyl ketone, gives the solid inorganic salt if that form is desired.

To produce an amine salt, the acid of formula I is dissolved in a suitable solvent of either moderate or lower polarity, for example, ethanol, methanol, ethyl acetate, diethyl ether and benzene. At least an equivalent amount of the amine corresponding to the desired cation is then added to that solution. If the resulting salt does not precipitate, it can usually be obtained in solid form by addition of a miscible diluent of low polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid of formula I with an equivalent amount of the corresponding quaternary ammonium hydroxide in water solution, followed by evaporation of the water.

The basic compounds of formula I in which $R^1$, $R^2$, $R^3$, $R^4$, $R^5$ and/or $R^6$ is $NR^7R^8$ wherein $R^7$ and $R^8$ are as defined herein or a radical of formula $Y-CR^9R^{10}-COOR^{11}$ wherein Y is $NR^{12}$ wherein $R^{12}$ is as defined herein, $R^9$ and $R^{10}$ are hyrogen and $R^{11}$ is lower alkyl form addition salts with suitable inorganic and organic acids. These salts possess the same activities as the parent base compound when administered to a mammal and may be utilized in the same manner. Suitable acids to form these salts include, for example, the common mineral acids, hydrohalic, sulfuric or phosphoric, as well as the organic acids, formic, acetic, maleic, malic, citric, or tartaric acid, or acids which are sparingly soluble in body fluids and which impart slow-release properties to their respective salts such as pamoic or tannic acid or carboxymethyl cellulose. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

Also included within the scope of this invention are the isomers of the compounds of formula I resulting from the asymmetric centers contained therein.

The tautomeric forms of the compounds of formula I in which $R^1$, $R^2$, $R^3$, $R^4$, $R^5$ and/or $R^6$ is hydroxy, resulting from the keto-enol equilibrium contained therein, are also included within the scope of this invention.

Anti-allergic Activity

The compounds of this invention of formula I, or therapeutically acceptable salts thereof, are useful in the prevention or treatment of allergic reactions in a mammal upon oral or parenteral administration.

More specifically, the compounds of this invention are useful for the prophylactic treatment as well as for the management of anaphylatic reactions and atopic allergic manifestations, for example, bronchial asthma, hay fever, allergic rhinitis, allergic conjunctivitis, food allergies, urticaria and the like, in a sensitized mammal.

More specifically exemplified, the compounds of this invention are effective anit-allergic agents when tested using the passive cutaneous anaphylaxis (PCA) method, described by I. Mota, Immunology, 7, 681 (1964). The anti-allergic activity of a given compound is measured in rats by its ability to inhibit the increase in vascular permeability at the site of injection of rat immunoglobulin E (IgE) followed by i.v. administration of the specific antigen. Evans blue is injected i.v. at the same time as the specific antigen and the size of the wheal or of the area infiltrated with Evans blue is measured and compared with that of untreated controls. An effective anti-allergic agent will prevent or inhibit the release of inflammatory mediators (mainly serotonin and histamine from the mast cells) which causes an increase in vascular permeability and thus an infiltration of Evans blue surrounding the site of injection of IgE.

The anti-allergic activity of the compounds of formula I is demonstrated by the reduction of the wheal size of sensitized skin tissue compared to that of control animals. A comparison of the anti-allergic activity of a standard compound, such as disodium cromoglycate, indicates that the compounds of this invention function in the same manner as disodium cromoglycate by blocking the release of mediators from the mast cells responsible for the allergic reaction.

When the compounds of formula I of this invention are used for suppressing allergic manifestations of anaphylatic reactions and atopic immediate hypersenitivity in a mammal, they are used alone or in combination with pharmacologically acceptable carriers, the proportion of which is determined by the solubility and the chemical nature of the compound, chosen route of administration and standard biological practice. For example, they are administered parenterally by injection; orally; by the nasal route, for instance, as drops or aerosol; by inhalation from an aerosol; or as a suppository.

In addition, the compounds of this invention can be administered in conjunction with common anti-allergics, for example, known compounds effecting anti-histaminic, analgesic, central nervous system depressant, anti-hypertensive, immunosuppressive, anti-bradykinin, anti-serotonin or endocrinological responses.

Therapeutic compositions containing the compounds of this invention are effective anti-allergic agents for preventing or relieving atopic allergic manifestations at dosages of 0.1 mg to 100 mg/kg body weight when administered parenterally to a mammal. For administration to a mammal by parenteral injection it is preferred to use the compounds of formula I in solution in a sterile aqueous vehicle which may also contain other solutes such as buffers or preservatives, as well as sufficient quantities of pharmaceutically acceptable salts or of glucose to make the solution isotonic.

A number of the compounds of this invention of formula I are useful in the management of allergic reactions when administered orally at dosages of 0.5 mg to 500 mg/kg body weight to a sensitized mammal. For example, the representative compound of formula I, [3-[N-(2-ethoxy-1,2-dioxoethyl)-N-methylamino]-2-oxo-3,5,7-cycloheptatrien-1-yl]amino]oxo-acetic acid ethyl ester (see Example 3) is an effective anti-allergic agent when administered orally at dosages of 30 mg to 100 mg/kg body weight.

When the compounds of this invention are employed as antiallergic agents in mamals, e.g. rats, the orally effective, antiallergic amounts of the compounds are administered to the mammal, either alone or combined with pharmaceutically acceptable excipients in a dosage form, i.e. capsule or tablet, or the compounds are administered orally in the form of solutions or suspensions.

The tablet compositions contain the active ingredient in admixture with non-toxic pharmaceutical excipients known to be suitable in the manufacture of tablets. Suitable pharmaceutical excipients are, for example, starch, milk sugar, certain types of clay and so forth. The tablets may be uncoated or they may be coated by known techniques so as to delay disintegration and absorption in the gastrointestinal tract and thereby provide a sustained action over a longer period.

The aqueous suspensions of the invention contain the active ingredient in admixture with one or more non-toxic pharmaceutical excipients known to be suitable in the manufacture of aqueous suspensions. Suitable excipients are, for example, methylcellulose, sodium alginate, gum acacia, lecithin and so forth. The aqueous suspensions may also contain one or more preservatives, one or more coloring agents, one or more flavoring agents and one or more sweetening agents.

Non-aqueous suspensions can be formulated by suspending the active ingredient in a vegetable oil, for example, arachis oil, olive oil, sesame oil, or coconut oil, or in a mineral oil, for example liquid paraffin, and the suspension may contain a thickening agent, for example beeswax, hard paraffin or cetyl alcohol. These compositions can also contain a sweetening agent, a flavoring agent and an anti-oxidant.

The compounds of formula I can also be administered as nasal powders or insufflations. For such purpose the compounds are administered in finely divided solid form together with a pharmaceutically acceptable solid carrier, for example, a finely divided polyethylene glycol ("Carbowax 1540") or finely divided lactose. Such compositions may also contain other excipients in finely divided solid form, for instance preservatives, buffers, or surface active agents.

When administering the compounds of this invention by inhalation from an aerosol, the compound of formula I is dissolved in water or ethanol and mixed with a volatile propellant, for example, dichlorotetrafluoroethane and dichlorodifluoromethane, and placed in a pressurized container having a metering valve to release a predetermined amount of material.

The dosage of the compounds of this invention will vary with the form of administration and the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstance is reached. In general, the compounds of this invention are most desirably administered at a concentration level that will generally afford effective results without causing any harmful or deleterious side effects, and preferably at a level that is in a range of from about 0.1 mg to about 500 mg per kilogram body weight, although as aforementioned variations will occur. However, a dosage level that is in the range of from about 0.5 mg to about 200 mg per kilogram body weight is most desirably employed in order to achieve effective results.

Processes

Useful and practical starting materials for the preparation of the compounds of this invention of formula I are the tropone derivatives of formula II

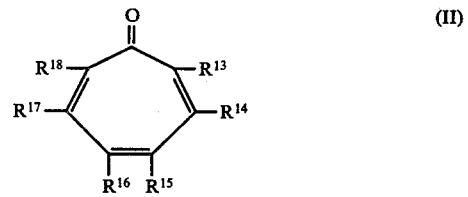

in which $R^{13}$, $R^{14}$, $R^{15}$, $R^{16}$, $R^{17}$ and $R^{18}$ are as defined herein.

The tropone derivatives of formula II suitable as starting materials are described in a number of reports, for example, see the recent review on tropone derivatives, their preparation and their interconversions by F. Pietra, supra. Thus, the tropone derivatives suitable as starting materials are either known or they can be prepared by conventional means.

The compounds of this invention of formula I are prepared by the following processes.

In practicing the condensation of the compound of formula II with the compound of formula III, as noted above, one to ten molar equivalents, preferably one to three molar equivalents, of the compound of formula III are used. The reaction medium for the condensation is preferably an inert solvent. Suitable solvents include benzene, toluene, chloroform, methylene chloride, lower alkyl ketones (i.e. 2-propanone, 2-butanone and 3-pentanone) and the like. However, if the reactants are mutually soluble, the solvent can be omitted without deleterious effects.

The preferred proton acceptors include the organic bases or amines, for instance, triethylamine, pyridine, N-ethylmorpholine, 1,5-diazabicyclo(3.4.0)-nonene-5 and the like, as well as the inorganic bases, preferably the alkali metal hydroxides, carbonates, hydrides, amides and alkoxides, for example, sodium ethoxide sodium hydroxide, potassium hydroxide, potassium carbonate, sodium methoxide and the like. The choice of the particular proton acceptor depends upon the reaction conditions as well as the nature of the particular condensation. For example, the preferred proton acceptors employed for the preparation of the compounds of formula I in which $R^1$, $R^2$, $R^3$, $R^4$, $R^5$ and/or $R^6$ is Y-$CR^9R^{10}$-$COOR^{11}$ wherein Y is O are the strong inorganic bases, for instance the alkali metal alkoxides, hydrides and amides, preferably, sodium ethoxide, sodium methoxide, sodium amide, potassium t-butoxide and the like. In the latter condensation the preferred amount of the strong inorganic base is about 1.0 to 1.3 molar equivalents. For the preparation of the compounds of formula I in which $R^1$, $R^2$, $R^3$, $R^4$, $R^5$ and/or $R^6$ is Y-$CR^9R^{10}$-$COOR^{11}$ wherein Y is S or $NR^{12}$ the preferred proton acceptors employed are the organic bases or amines. The amount of the organic base can vary from one molar equivalent to a large molar excess. When a large molar excess of an organic base is used, the organic base can also serve as the solvent for the condensation.

The duration and temperature of the condensation are not critical; however, the preferred time is from about ten minutes to about two days and the temperature can range from about $-10°$ C to about $100°$ C or the boiling point of the reaction mixture. The compounds of formula I are separated from the reaction mixture by conventional means, for example, evaporation, filtration, extraction, chromatography and/or crystallization.

In another embodiment of the process of this invention, the compound of formula II is condensed with the compound of formula V, as noted above. The required amount of the compound of formula V is from one to ten molar equivalents, preferably one to three molar equivalents.

Suitable solvents, reaction conditions and proton acceptors, preferably organic bases for the latter condensation can be selected from those described for the former condensation of the compound of formula II and the compound of formula III.

The compounds of formula I, and the intermediates of formula IV, obtained from the above described condensations, can be further reacted to obtain other compounds of formula I by methods described hereinafter.

For instance, the above described compound of formula IV in which at least one of $R^{19}$, $R^{20}$, $R^{21}$, $R^{22}$, $R^{23}$ and $R^{24}$ is a radical of formula Y-$CR^9R^{10}$-$COOR^{11}$ wherein $R^9$ and $R^{10}$ are hydrogen, $R^{11}$ is lower alkyl and Y is S is oxidized with substantially one molar equivalent of an oxidizing agent, preferably an organic peracid, for example, meta-chloroperbenzoic acid, perbenzoic acid and the like, or hydrogen peroxide, to obtain the corresponding compound of formula I in which the corresponding $R^1$, $R^2$, $R^3$, $R^4$, $R^5$ and $R^6$ is a radical of formula Y-$CR^9R^{10}$-$COOR^{11}$ wherein $R^9$ and $R^{10}$ are hydrogen and $R^{11}$ is lower alkyl and Y is SO. In the same manner, the use of substantially two to five molar equivalents of the oxidizing agent gives the corresponding compound of formula I in which the corresponding $R^1$, $R^2$, $R^3$, $R^4$, $R^5$ and $R^6$ is a radical of formula Y-$CR^9R^{10}$-$COOR^{11}$ wherein $R^9$, $R^{10}$ and $R^{11}$ are as defined immediately above and Y is $SO_2$. The above oxidations are preferably effected in an inert organic solvent, for example a haloalkane, i.e., chloroform, methylene chloride, trichloroethane and the like, at a temperature ranging from about $-10°$ C to about $60°$ C for about 10 minutes to about 5 hours.

In some cases it is convenient and preferable to prepare a specific compound of formula I by the transformation of another compound of formula I. Examples of such interconversions of the compound of formula I are described hereinafter.

The compound of formula I, prepared as described above, in which at least one of $R^1$, $R^2$, $R^3$, $R^4$, $R^5$ and $R^6$ is a radical of formula Y-$CR^9R^{10}$-$COOR^{11}$ wherein $R^9$, $R^{10}$ and Y are as described herein and $R^{11}$ is lower alkyl can be hydrolyzed to obtain the corresponding acidic compound of formula I in which the corresponding $R^1$, $R^2$, $R^3$, $R^4$, $R^5$ and $R^6$ is a radical of formula Y-$CR^9R^{10}$-$COOR^{11}$ wherein $R^9$, $R^{10}$ and Y are as defined herein and $R^{11}$ is hydrogen. The preferred method of hydrolysis comprises the use of 0.1 to 2.0 molar equivalents, preferably 0.5 to 1.0 molar equivalents, of a mild alkali, for example a suitable mild alkali selected from the bicarbonates and acetates of sodium or potassium, in an inert solvent, for instance, water, a lower alkanol (i.e. methanol or ethanol) or mixtures thereof, at a temperature of about $20°$ C to $120°$ C for about 1 to 10 hours. Acidification of the reaction mixture with a dilute mineral acid, such as hydrochloric acid, sulfuric acid, phosphoric acid and the like, gives the corresponding acidic compound of formula I.

The acidic compound of formula I described above (i.e. $R^{11}$ is hydrogen) is readily esterified to obtain the corresponding ester of formula I (i.e., $R^{11}$ is lower alkyl). Suitable esterification conditions include a variety of methods; for example, ester exchange, treatment with diazomethane, or conversion of the acid to the corresponding activated carbonyl (i.e., acid halide, anhydride, succinimido, imidazolide and the like) followed by treatment of the latter with an appropriate lower alkanol, see also, L.F. Fieser and M. Fieser, "Advanced Organic Chemistry", Reinhold Publishing Corporation, New York 1961, pp. 370-381.

A preferred and convenient method of esterification comprises dissolving the acidic compound of formula I in an inert solvent, preferably dimethylsulfoxide, in the presence of one to ten molar equivalents of a mild base, for example, sodium or potassium carbonate. One to three molar equivalents of a lower alkyl bromide or chloride is added and the solution is maintained at a temperature of about $20°$ C to $100°$ C, preferably at about $40°$ C to $80°$ C, for about 30 minutes to five hours.

The compound of formula I in which at least one of $R^1$, $R^2$, $R^3$, $R^4$, $R^5$ and $R^6$ is hydroxy can be alkylated to obtain the corresponding compound of formula I in which the corresponding $R^1$, $R^2$, $R^3$, $R^4$, $R^5$ and $R^6$ is alkoxy. The alkylation is conveniently carried out by reacting the hydroxy compound with one to five molar equivalents of a di(lower)alkyl sulfate, for example dimethyl or diethyl sulfate, in the presence of one to five molar equivalents of a mild alkali, for instance sodium or potassium carbonate, in an inert solvent, for example, a lower alkyl ketone, preferably 2-butanone, 2-propanone and the like. The alkylation is conducted at a temperature from about 30° C to the boiling point of the reaction mixture for about 30 minutes to ten hours.

A useful alternative method of alkylation comprises reacting the hydroxy compound of formula I with an excess of a diazoalkane, for instance diazoethane and the like, in an inert solvent, e.g. diethyl ether or methanol.

The compound of formula I in which at least one of $R^1$, $R^2$, $R^3$, $R^4$, $R^5$ and $R^6$ is lower alkoxy, chlorine, bromine or iodine can be reacted with a molar excess of ammonia or an amine of formula $HNR^7R^8$ in which $R^7$ and $R^8$ are as defined herein to obtain the corresponding compound of formula I in which at least one of $R^1$, $R^2$, $R^3$, $R^4$, $R^5$ and $R^6$ is $NR^7R^8$ wherein $R^7$ and $R^8$ are as defined herein. A suitable solvent for the reaction can be selected from the amine, water and a lower alkanol (i.e. methanol, ethanol and the like). Suitable conditions for the reaction are a temperature of from about $-50°$ C to about 100° C, preferably 0° C to 100° C, for about 10 minutes to 12 hours. If the temperature necessary for the reaction is above the boiling point of the reaction mixture, the reaction can be conducted at the desired temperature in a sealed pressure vessel without deleterious effects.

Similarly the compound of formula I in which at least one of $R^1$, $R^2$, $R^3$, $R^4$, $R^5$ and $R^6$ is lower alkoxy, chlorine, bromine or iodine can be reacted with sodium sulfhydrate in an inert solvent, preferably a lower alkanol, i.e. methanol or ethanol, to obtain the corresponding compound of formula I in which the corresponding $R^1$, $R^2$, $R^3$, $R^4$, $R^5$ and $R^6$ is mercapto. This reaction is preferably carried out at a temperature of from about $-70°$ C to about 30° C for 1 to 10 hours.

The above described processes can be followed to prepare other compounds of formula I in which $R^1$ and $R^2$, $R^2$ and $R^3$, $R^3$ and $R^4$, $R^4$ and $R^5$ or $R^5$ and $R^6$ are joined together with a chain selected from the group consisting of —CH=CH—CH=CH—, —C=CH—N=CH— and —(CH$_2$)$_n$— wherein n is an integer from 1 to 10 and $R^3$, $R^4$, $R^5$ and $R^6$; $R^1$, $R^4$, $R^5$ and $R^6$; $R^1$, $R^2$, $R^5$ and $R^6$, $R^1$, $R^2$, $R^3$ and $R^6$ or $R^1$, $R^2$, $R^3$ and $R^4$, respectively, are as defined herein.

It should be understood that the invention as disclosed herein would also include compounds of formula I in which $R^1$, $R^2$, $R^3$, $R^4$, $R^5$ and $R^6$ are the same or different selected from the group consisting of hydrogen; halo; trifluoromethyl; lower alkoxy; lower alkyl; phenyl; hydroxy; phenoxy; mercapto; $NR^7R^8$ wherein each of $R^7$ and $R^8$ is hydrogen or lower alkyl; and a radical of formula Y-$CR^9R^{10}$-$COOR^{11}$ wherein Y is O, S or $NR^{12}$ wherein $R^{12}$ is hydrogen or lower alkyl, $R^9$ and $R^{10}$ together are oxo and $R^{11}$ is hydrogen or lower alkyl, or Y is SO or SO$_2$, $R^9$ and $R^{10}$ are hydrogen and $R^{11}$ is hydrogen or lower alkyl; with the proviso that one, two or three of $R^1$, $R^2$, $R^3$, $R^4$, $R^5$ and $R^6$ must be a radical of formula Y-$CR^9R^{10}$-$COOR^{11}$ wherein Y, $R^9$, $R^{10}$ and $R^{11}$ are as defined herein; and with the additional proviso when one of $R^1$ or $R^4$ is a radical of the formula Y-$CR^9R^{10}$-$COOR^{11}$ wherein Y is $NR^{12}$ wherein $R^{12}$ is as defined herein, $R^9$ and $R^{10}$ together as oxo and $R^{11}$ is as defined herein, then $R^4$ or $R^1$ respectively is a radical of the formula Y-$CR^9R^{10}$-$COOR^{11}$ wherein Y is O or S, $R^9$ and $R^{10}$ together are oxygen and $R^{11}$ is hydrogen or lower alkyl, or Y is SO or SO$_2$, $R^9$ and $R^{10}$ are hydrogen and $R^{11}$ is hydrogen or lower alkyl and $R^2$, $R^3$, $R^5$ and $R^6$ are as defined herein.

The following examples illustrate further this invention.

EXAMPLE 1

2-Mercapto-2,4,6-cycloheptatrien-1-one

A solution of 2-chloro-2,4,6-cycloheptatrien-1-one [2.82 g, described by T. Nozoé et al., Proc. Japan Acad., 28, 483 (1952)] in ethanol (20 ml) is added dropwise to a suspension, cooled to $-70°$ C, of sodium sulfhydrate (2.2 g.) in ethanol (20 ml). The mixture is stirred at $-70°$ C for 2 hours, allowed to warm to room temperature and stirred at room temperature for one hour. The mixture is filtered and the filtrate is evaporated. The residue is suspended in water, the mixture is acidified to pH2 with 10% hydrochloric acid and extracted with ethyl acetate. The organic extract is dried and evaporated. The residue is dissolved in benzene and subjected to chromatography on silica gel. The eluates are evaporated to give the title compound, mp 55° C.

EXAMPLE 2

[(2-Oxo-3,5,7-cycloheptatrien-1-yl)thioloxo-acetic Acid Ethyl Ester; I ($R^1$ = S-CO-COOC$_2$H$_5$; $R^2$, $R^3$, $R^4$, $R^5$, and $R^6$ = H)

A solution of ethyl oxalyl chloride (0.58 ml) in methylene chloride (4 ml) is added to a solution of 2-mercapto-2,4,6-cycloheptatrien-1-one (0.584 g described in Example 1) and triethylamine (0.66 ml) in methylene chloride (5 ml) and the mixture is stirred at room temperature for 30 minutes. The reaction mixture is diluted with methylene chloride, washed with water, dried and evaporated. The residue is suspended in methanol, filtered and the filtrate is evaporated to give the title compound; nmr (CDCl$_3$) δ1.4 (+, 3H), 4.4 (q, 2H), 7.15 (m, 4H) and 7.85 (M, 1H).

In the same manner but replacing ethyl oxalyl chloride with an equivalent amount of methyl oxalyl chloride, the methyl ester of the title compound is obtained.

By following serially the procedures of Examples 1 and 2 but replacing 2-mercapto-2,4,6-cycloheptatrien-1-one with an equivalent amount of 5-mercapto-7H-benzocyclohepten-7-one, 9-amino-7H-cyclohepta[c]pyridin-7-one, 5-mercapto-3H-6,7-dihydrocyclobutacyclohepten-3-one, 1-ethylamino-3H-6,7,8,9,10,11-hexahydrocycloheptacycloocten-3-one and 5-mercapto-3H-6,7,8,9,10,11,12,13-octahydrocycloheptacycodecen-3-one, the following compounds are obtained respectively: [(7-oxo-7H-benzocyclohepten-5-yl)thio]oxoacetic acid ethyl ester (I: $R^1$, $R^5$, and $R^6$ = H; $R^2$ = S-CO-COOC$_2$H$_5$; and $R^3$ and $R^4$ together form a —CH=CH—CH=CH— chain), [(7-oxo-7H-cyclohepta[c]pyridin-9-yl)-amino]oxo-acetic acid ethyl ester (I: $R^1$, $R^5$ and $R^6$ = H; $R^2$ = NC$_2$H$_5$-CO-COOC$_2$H$_5$; and $R^3$ and $R^4$ together form a —CH=CH—N=CH— chain). [(3-oxo-3H-6,7-dihydrocyclobutacyclohepten-5-yl)thio]oxo-acetic acid ethyl ester (I; $R^1$, $R^5$ and $R^6$ = H; $R^2$ = S-CO-COOC$_2$H$_5$; and $R^3$ and $R^4$ together form a -CH$_2$CH$_2$- chain), [N-(3-oxo-3H-6,7,8,9,10,11-hexahydrocycloheptacycloocten-1-yl)ethylamino]-oxo-acetic acid ethyl ester (I; $R^1$, $R^2$ and $R^6$ = H; $R^3$ and $R^4$ together form a -(CH$_2$)$_6$ chain; and R$^5$ = NC$_2$H$_5$-CO-COOC$_2$H$_5$) and [(3-oxo-3H-6,7,8,9,10,11,12,13-octahydrocycloheptacyclodecen-5-yl)thio]oxoacetic acid ethyl ester (I; R$^1$, R$^5$ and R$^6$ = H; R$^2$ = S-CO-COOC$_2$H$_5$; and R$^3$ and R$^4$ together form a —(CH$_2$)$_8$— chain).

EXAMPLE 3

[[3-[N-(2-Ethoxy-1,2-dioxoethyl)-N-methylamino]-2-oxo-3,5,7-cycloheptatrien-1-yl]amino]oxo-acetic Acid Ethyl Ester; 1; (R$^1$ = NH-CO-OOOC$_2$H$_5$; R$^2$, R$^3$, R$^4$ and R$^5$ = H and R$^6$ = N(CH$_3$)-CO-COOC$_2$H$_5$)

A mixture of 2-hydroxy-3-[[(4-methylphenyl)sulfonyl]amino]-2,4,6-cycloheptatrien-1-one [14.5 g, described by Y. Kitahara, Science Repts. Tohoku Univ. Ser. 1, 40, 83 (1956)] dimethyl sulfate (12.5 g), potassium carbonate (12.5 g) and 2-butanone (145 ml) is heated at reflux for 1 hour. The mixture is filtered and the filtrate is evaporated. The residue is subjected to chromatography on silica gel using hexane-ethyl acetate (1:3). The eluates are concentrated to obtain crystals of 2-methoxy-7-[N-[(4-methylphenyl)sulfonyl]-N-methylamino]-2,4,6-cycloheptatrien-1-one, mp 94.5° C.

A solution of the latter compound (4.0 g) in methanol (40 ml) is cooled to —25° C and saturated with ammonia gas. The solution in a pressure bottle is heated at 80° C for 4 hours and cooled to —70° C. The bottle is opened and the solution evaporated to give 2-amino-7-[N-[(4-methylphenyl)sulfonyl]-N-methylamino]-2,4,6-cycloheptatrien-1-one, mp 221°-222° C.

A solution of the latter compound (2.53 g) in conc. sulfuric acid (25 ml) is heated at 70° C for 1 hour and added to ice. The ice-mixture is neutralized with sat. sodium carbonate solution and extracted with chloroform. The organic extract is dried over sodium sulfate and evaporated to give 2-amino-7-methylamino-2,4,6-cycloheptatrien-1-one.

A solution of ethyl oxalyl chloride (2.46 g) in methylene chloride (10 ml) is added dropwise to a solution of 2-amino-7-methylamino-2,4,6-cycloheptatrien-1-one (1.32 g) and triethylamine (1.95 g) in methylene chloride (15 ml). The mixture is heated at reflux for 3 hours, washed with water, dried over sodium sulfate and evaporated. The residue is subjected to chromatography on silica gel using acetone-hexane (3:7) and the eluates are evaporated to give the title compound, nmr (trifluoroacetic acid) δ 1.5 (m, 6H), 3.45 (s, 3H), 4.55 (m, 4H) and 7.6 – 9.2 ppm (m, 4H).

By following a procedure selected from Example 2 or 3 using the appropriate starting material of formula II and the appropriate compound of formula III, such as methyl or ethyl oxayl chloride, other compounds of formula I in which at least one of R$^1$, R$^2$, R$^3$, R$^4$, R$^5$ and R$^6$ is Y-CR$^9$R$^{10}$-COOR$^{11}$ wherein Y is S or NR$^{12}$, R$^9$ and R$^{10}$ together are oxo and R$^{11}$ is methyl or ethyl are obtained. Examples of the latter compounds of formula I are listed as products in Table I together with the appropriate starting material of formula II used for the preparation of the compound of formula I.

TABLE 1

| EXAMPLE | STARTING MATERIAL OF FORMULA 11 | | | | | | PRODUCT |
| --- | --- | --- | --- | --- | --- | --- | --- |
| | R$^1$ | R$^2$ | R$^3$ | R$^4$ | R$^5$ | R$^6$ | |
| 4 | CH$_3$ | Br | H | H | NH$_2$ | H | [(5-bromo-4-methyl-3-oxo-1,4,6-cycloheptatrien-1-yl)amino]-oxo-acetic acid ethyl ester |
| 5 | H | NH$_2$ | OC$_6$H$_5$ | H | H | 1 | [(4-iodo-3-oxo-7-phenoxy-1,4,6-cycloheptatrien-1-yl)amino]-oxo-acetic acid methyl ester |
| 6 | H | CH$_3$ | NH(C$_3$H$_7$) | H | NH$_2$ | H | [[6-[N-(2-ethoxy-1,2-dioxoethyl)methylamino]-5-methyl-1,4,6-cycloheptatrien-1-yl]amino]oxo-acetic acid ethyl ester |
| 7 | CF$_3$ | NH$_2$ | H | H | C$_3$H$_7$ | H | [(3-oxo-5-propyl-2-trifluoromethyl-1,4,6-cycloheptatrien-1-yl)amino]oxo-acetic acid ethyl ester |
| 8 | H | Br | H | SH | H | SH | 2,2'-[(4-bromo-2-oxo-3,5,7-cycloheptatrien-1-yl)bis(thio)]-bis[2-oxo-acetic acid]diethyl ester |
| 9 | H | N(CH$_3$)$_2$ | Cl | H | NH$_2$ | H | [(6-chloro-5-dimethylamino-3-oxo-1,4,6-cycloheptatrien-1-yl)amino]oxo-acetic acid ethyl ester |
| 10 | SH | H | H | CF$_3$ | H | C$_6$H$_{13}$ | [(3-hexyl-2-oxo-6-trifluoromethyl-3,5,7-cycloheptatrien-1-yl)thio]oxo-acetic acid methyl ester |
| 11 | NH$_2$ | H | H | C$_2$H$_5$ | H | NH$_2$ | 2,2'-[(5-ethyl-2-oxo-3,5,7-cycloheptatrien-1-yl)diimino]-bis[2-oxo-acetic acid]dimethyl ester |
| 12 | H | OCH$_3$ | H | C$_6$H$_5$ | SH | H | [(5-methoxy-7-phenyl-3-oxo-1,4,6-cycloheptatrien-1-yl)thio]oxo-acetic acid ethyl ester |
| 13 | NH$_2$ | H | NH$_2$ | H | H | NH$_2$ | 2,2''[(2-oxo-3,5,7-cycloheptatriene-1,3,6-triyl)-triimino]tris[2-oxo-acetic acid]triethyl ester |
| 14 | H | H | SH | C$_3$H$_7$ | H | OC$_6$H$_5$ | [(4-oxo-5-phenoxy-7-propyl-2,5,7-cycloheptatrien-1-yl)thio]-oxo-acetic acid ethyl ester |
| 15 | H | Br | N(C$_2$H$_5$)$_2$ | SH | H | Br | [(3,6-dibromo-7-diethylamino-4-oxo-2,5,7-cycloheptatrien-1-yl)thio]oxo-acetic acid ethyl ester |
| 16 | SH | H | CF$_3$ | H | C$_5$H$_{11}$ | H | [(2-oxo-4-pentyl-6-trifluoromethyl-3,5,7-cycloheptatrien-1-yl)thio]oxo-acetic acid methyl ester |
| 17 | SH | H | H | H | OC$_3$H$_7$ | NH$_2$ | [[3-[(2-ethoxy-1,2-dioxoethyl)thio]-7-propoxy-3,5,7-cycloheptatrien-1-yl]amino]oxo-acetic acid ethyl ester |
| 18 | OC$_6$H$_5$ | H | SH | H | H | CF$_3$ | [(5-oxo-4-phenoxy-6-trifluoromethyl-1,3,6-cycloheptatrien-1-yl)thio]oxo-acetic acid methyl ester |
| 19 | H | H | H | NH$_2$ | H | NH$_2$ | 2,2'-[(2-oxo-3,5,7-cycloheptatriene-1,6-diyl)diimino]bis-[2-oxo-acetic acid]diethyl ester |
| 20 | H | NHC$_3$H$_7$ | H | I | OH | H | [N-(4-hydroxy-3-iodo-6-oxo-2,4,7-cycloheptatrien-1-yl)-N-propylamino]oxo-acetic acid ethyl ester |
| 21 | OH | H | N(C$_2$H$_5$)$_2$ | H | SH | H | [(3-diethylamino-5-hydroxy-6-oxo-2,4,7-cycloheptatrien-1-yl)thio]oxo-acetic acid ethyl ester |

EXAMPLE 22

[(2-Oxo-3,5,7-cycloheptatrien-1-yl)oxy]oxo-acetic Acid Ethyl Ester; I (R$^1$ = O-CO-COOC$_2$H$_5$; R$^2$, R$^3$, R$^4$, R$^5$ and R$^6$ = H)

To a suspension of the sodium salt (4.27 g) of 2-hydroxy-2,4,6-cycloheptatrien-1-one (prepared from 2-hydroxy-2,4,6-cycloheptatrien-1-one described by H. C. Stevens et al., Jour. Org. Chem., 36, 2780 (1971) and sodium ethoxide 1:1 equivalents) in benzene (10 ml) is added a solution of ethyl oxalyl chloride (3.3 ml) in dry benzene (15 ml). The mixture is stirred at room temperature for 1.5 hours, diluted with ether and filtered. The filtrate is flushed twice with benzene and dried under reduced pressure to give the title compound as an oil;

nmr (CDCl₃) δ 1.35 (+, 3H), 4.39 (q, 2H) and 7.25 (m, 5H).

In the same manner but replacing sodium ethoxide with an equivalent amount of sodium methoxide, sodium amide or potassium ±-butoxide, the title compound is obtained.

$CR^9R^{10}$-$COOR^{11}$ wherein Y is O, $R^9$ and $R^{10}$ together are oxo and $R^{11}$ is methyl or ethyl are obtained. Examples of the latter compounds of formula I are listed as products in Table II together with the appropriate starting material of formula II used for the preparation of the compound of formula I.

TABLE II

| EX. | $R^1$ | $R^2$ | $R^3$ | $R^4$ | $R^5$ | $R^6$ | PRODUCT |
|---|---|---|---|---|---|---|---|
| 23 | CH₃ | H | Br | H | H | OH | [(5-bromo-3-methyl-2-oxo-3,5,7-cycloheptatrien-1-yl)oxy]-oxo-acetic acid ethyl ester |
| 24 | H | OC₆H₅ | H | OH | H | H | [(4-oxo-3-phenoxy-2,5,7-cycloheptatrien-1-yl)oxy]oxo-acetic acid ethyl ester |
| 25 | H | N(C₄H₉)₂ | H | I | OH | H | [(5-dibutylamino-3-oxo-1,4,6-cycloheptatrien-1-yl)oxy]-oxo-acetic acid methyl ester |
| 26 | CH₃ | H | OH | CH₃ | H | C₆H₁₃ | [(3,7-dimethyl-5-hexyl-2,5,7-cycloheptatrien-1-yl)oxy]oxo-acetic acid methyl ester |
| 27 | Cl | H | H | OH | H | OH | [(5-chloro-4-oxo-2,5,7-cycloheptatrien-1,3-diyl)bis(oxy)]-bis[2-oxo-acetic acid]diethyl ester |
| 28 | H | OH | Br | H | OC₃H₇ | H | [(7-bromo-3-oxo-5-phenoxy-1,4,6-cycloheptatrien-1-yl)oxy]-ox-acetic acid ethyl ester |
| 29 | OH | H | CH(CH₃)C₃H₇ | H | C₂H₅ | H | [[4-ethyl-6-(1-methylbutyl)-2-oxo-3,5,7-cycloheptatrien-1-yl]oxy]oxo-acetic acid ethyl ester |
| 30 | H | C₆H₅ | OH | H | N(CH₃)₂ | H | [(6-dimethylamino-4-oxo-2-phenyl-4-oxo-2,5,7-cycloheptatrien-1-yl)oxy]oxo-acetic acid ethyl ester |
| 31 | H | CF₃ | H | OC₄H₉ | H | OH | [(6-butoxy-2-oxo-4-trifluoromethyl-3,5,7-cycloheptatrien-1-yl)oxy]oxo-acetic acid methyl ester |
| 32 | OH | H | H | OH | H | OH | [(2-oxo-3,5,7-cycloheptatriene-1,3,5-triyl)tris(oxy)[-tris]2-oxo-acetic acid]trimethyl ester |
| 33 | H | N(C₃H₇)₂ | H | C₂H₅ | H | OH | [(4-dipropylamino-6-ethyl-2-oxo-3,5,7-cycloheptatrien-1-yl)oxy]oxo-acetic acid ethyl ester |
| 34 | CH₃ | CH₃ | OH | H | H | C₂H₅ | [(2,3-dimethyl-5-ethyl-4-oxo-2,5,7-cycloheptatrien-1-yl)-oxy]oxo-acetic acid methyl ester |
| 35 | C₆H₅ | OCH₃ | H | OH | H | CF₃ | [(6-methoxy-4-oxo-5-phenyl-3-trifluoromethyl-2,5,7-cycloheptatrien-1-yl)oxy]oxo-acetic acid ethyl ester |
| 36 | H | H | C₅H₁₁ | OCH₂C(CH₃)₂ | OH | H | [[7-(2-methylpropyloxy)-3-oxo-6-pentyl-1,4,6-cycloheptatrien-1-yl]oxy]oxo-acetic acid ethyl ester |
| 37 | H | H | OH | H | H | OH | [(2-oxo-3,5,7-cycloheptatriene-1,5-diyl)bis(oxy)]bis[2-oxo-acetic acid]diethyl ester |
| 38 | OH | H | CF₃ | H | OC₆H₅ | H | [(4-phenoxy-2-oxo-6-trifluoromethyl-3,5,7-cycloheptatrien-1-yl)oxy]oxo-acetic acid methyl ester |
| 39 | H | OH | H | Br | N(CH₃)₂ | H | [(6-bromo-5-dimethylamino-3-oxo-1,4,6-cycloheptatrien-1-yl)oxy]oxo-acetic acid methyl ester |

In the same manner using the appropriate compound of formula III and replacing 2-hydroxy-2,4,6-cycloheptatrien-1-one with an equivalent amount of 5-hydroxy-7H-benzocyclohepten-7-one, 6-hydroxy-7H-cyclohepta[c]pyridin-7-one, 2-hydroxy-3H-6,7-dihydrocyclobutacyclohepten-3-one, 1-hydroxy-3H-6,7,8,9,10,11-hexahydrocycloheptacycloocten-3-one, and 2-hydroxy-3H-6,7,8,9,10,11,12,13-octahydrocycloheptacyclodecen-3-one, the following compounds are obtained respectively: [(7H-7-oxobenzocyclohepten-6-yl)oxy]oxo-acetic acid methyl ester (I; $R^1$, $R^5$ and $R^6$ = H, $R^3$ and $R^4$ together form a —CH=CH—CH=CH— chain and $R^2$ = O-CO-COOCH₃), [(7-oxo-7H-cyclohepta[c]pyridin-6-yl)oxy]oxo-acetic acid ethyl ester (1; $R^1$, $R^2$ and $R^5$ = H, $R^3$ and $R^4$ together form a —CH₂=CH₂—N=• CH— chain and $R^6$ = O-CO-COOC₂H₅), [(3-oxo-3H-6,7-dihydrocyclobutacyclohepten-2-yl)oxy]oxo-acetic acid ethyl ester (1; $R^2$, $R^5$ and $R^6$ = H, $R^3$ and $R^4$ together form a -CH₂-CH₂- chain and $R^1$ = O-CO-COOC₂H₅), [(3-oxo-3H-6,7,8,9,10,11-hexahydrocycloheptacycloocten-1-yl)oxy]oxo-acetic acid ethyl ester (1; $R^1$, $R^2$ and $R^6$ = H, $R^3$ and $R^4$ together form a —(CH₂)₆- chain and $R^5$ = O-CO-COOC₂H₅) and [(3H-6,7,8,9,10,11,12,13-octahydro-3-oxocycloheptacyclodecen-2-yl)oxy]oxo-acetic acid methyl ester (1; $R^1$, $R^2$ and $R^5$ = H, $R^3$ and $R^4$ together form a -(CH₂)₈- chain and $R^6$ = O-CO-COOCH₃).

By following the procedure of Example 22 using the appropriate starting material of formula II in which at least one of $R^1$, $R^2$, $R^3$, $R^4$, $R^5$ and $R^6$ is hydroxy and the appropriate compound of formula III, such as methyl or ethyl oxalyl chloride, other compounds of formula I in which at least one of $R^1$, $R^2$, $R^3$, $R^4$, $R^5$ and $R^6$ is Y-

EXAMPLE 40

[(2-Oxo-3,5,7-cycloheptatrien-1-yl)thio]acetic Acid Methyl Ester; IV ($R^{19}$ = S-CH₂-OOOCH₃; $R^{20}$, $R^{21}$, $R^{22}$, $R^{23}$ and $R^{24}$ = H)

A solution of the compound of formula IV, methyl mercaptoacetate (4.12 ml), in methylene chloride (40 ml) is added dropwise to a solution of the compound of formula II, 2-chloro-2,4,6-cycloheptatrien-1-one [5.6 g, described by T. Nozoe et al., Proc. Japan. Acad., 28. 483 (1952)], and triethylamine (6.12 ml) in methylene chloride (60 ml). After completion of the addition, the mixture is stirred at room temperature for 30 minutes. Methylene chloride is added and the solution is treated with charcoal and filtered. The filtrate is evaporated and the residue is crystallized from chloroformhexane to give the title compound, mp 71°–72° C.

In the same manner but replacing 2-chloro-2,4,6-cycloheptatrien-1-one with an equivalent amount of 4-bromo-7-methyl-2-phenoxy-2,4,6-cycloheptatrien-1-one, 6-chloro-2-hydroxy-4-diethylamino or 5-bromo-7-butyl-3-phenyl-2,4,6-cycloheptatrien-1-one, the corresponding compounds of formula IV [(5-oxo-4-phenoxy-6-methyl-1,3,6-cycloheptatrien-1-yl)thio]-acetic acid methyl ester, [(3-diethylamino-5-hydroxy-6-oxo-2,4,7-cycloheptatrien-1-yl)thio]acetic acid methyl ester and [(3-butyl-4-oxo-6-phenyl-2,5,7-cycloheptatrien-1-yl)thio]acetic acid methyl ester are obtained respectively.

EXAMPLE 41

[(2-Oxo-3,5,7-cycloheptatrien-1-yl)sulfino]acetic Acid Methyl Ester; I (R$^1$ = SO-CH$_2$-COOCH$_3$; R$^2$, R$^3$, R$^4$, R$^5$ and R$^6$ = H)

A solution of [(2-oxo-3,5,7-cycloheptatrien-1-yl)thio]acetic acid methyl ester (2.1 g, described in Example 40) in chloroform (15 ml) is added dropwise to a solution of 0° C of m-chloroperbenzoic acid (2.8 g) in chloroform (20 ml). The mixture is stirred at 0° C for 30 minutes and filtered. The filtrate is diluted with chloroform, washed with sodium bicarbonate solution and water, dried and evaporated. The residue is dissolved in ether-chloroform and filtered. The filtrate is evaporated and the residue is crystallized from chloroform-hexane to give the title compound, mp 101° C.

In the same manner but replacing m-chloroperbenzoic acid with an equivalent amount of perbanzoic acid the title compound is obtained.

In the same manner but replacing [(2-oxo-3,5,7-cycloheptatrien-1-yl)thio]acetic acid methyl ester with an equivalent amount of [(5-oxo-4-phenoxy-6-methyl-1,3,6-cycloheptatrien-1-yl)thio]acetic acid methyl ester, [(3-diethylamino-5-hydroxy-6-oxo-2,4,7-cycloheptatrien-1-yl)-thio]acetic acid methyl ester or [(3-butyl-4-oxo-6-phenyl-2,5,7-cycloheptatrien-1-yl)thio]acetic acid methyl ester, described in Example 40, [(5-oxo-4-phenoxy-6-methyl-1,3,6-cycloheptatrien-1-yl)sulfino]-acetic acid methyl ester, [(3-diethylamino-5-hydroxy-6-oxo-2,4,7-cycloheptatrien-1-yl)sulfino]-acetic acid ethyl ester and [(3-butyl-4-oxo-6-phenyl-2,5,7-cyclohpetatrien-1-yl)sulfino]-acetic acid methyl ester are obtained respectively.

EXAMPLE 42

[(2-Oxo-3,5,7-cycloheptatrien-1-yl)sulfono]acetic acid Methyl Ester; I (R$^1$ = SO$_2$-CH$_2$-COOCH$_3$; R$^2$, R$^3$, R$^4$, R$^5$ and R$^6$ = H)

A solution of [(2-oxo-3,5,7-cycloheptatrien-1-yl)thio]acetic acid methyl ester (1.75 g, described in Example 40) in chloroform (10 ml) is added dropwise to a solution at 0° C of m-chloroperbenzoic acid (2.3 g) in chloroform (15 ml). The mixture is stirred at 0° C for 5 minutes. m-Chloroperbenzoic acid (2.3 g) is added and the reaction mixture is heated at 50° C for one hour. The solution is diluted with chloroform, washed with sodium bicarbonate solution and water, dried and evaporated. The residue is crystallized from chloroformhexane to give the title compound, mp 117°–118° C.

In the same manner but replacing m-chloroperbenzoic acid with an equivalent amount of perbenzoic acid the title compound is obtained.

In the same manner but replacing [(2-oxo-3,5,7-cycloheptatrien-1-yl)thio]acetic acid methyl ester with an equivalent amount of [(5-oxo-4-phenoxy-6-methyl-1,3,6-cycloheptatrien-1-yl)thio]acetic acid methyl ester, [(3-diethylamino-5-hydroxy-6-oxo-2,4,7-cycloheptatrien-1-yl)thio]acetic acid methyl ester or [(3-butyl-4-oxo-6-phenyl-2,5,7-cycloheptatrien-1-yl)thio]acetic acid methyl ester, described in Example 40, [(5-oxo-4-phenoxy-6-methyl-1,3,6-cycloheptatrien-1-yl)sulfono]-acetic acid methyl ester, [(3-diethylamino-5-hydroxy-6-oxo-2,4,7-cycloheptatrien-1-yl)sulfono]-acetic acid ethyl ester and [(3-butyl-4-oxo-6-phenyl-2,5,7-cycloheptatrien-1-yl)sulfono]-acetic acid methyl ester are obtained respectively.

We claim:

1. A compound of formula I

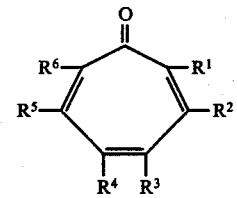

in which R$^1$, R$^2$, R$^3$, R$^4$, R$^5$ and R$^6$ are the same or different selected from the group consisting of hydrogen; halo, trifluoromethyl; lower alkoxy; lower alkyl; phenyl; hydroxy; phenoxy; mercapto; NR$^7$R$^8$ wherein each of R$^7$ and R$^8$ is hydrogen or lower alkyl; and a radical of formula Y-CR$^9$R$^{10}$-COOR$^{11}$ wherein Y is NR$^{12}$ wherein R$^{12}$ is hydrogen or lower alkyl, R$^9$ and R$^{10}$ together are oxo and R$^{11}$ is hydrogen or lower alkyl, with the proviso that one, two or three of R$^1$, R$^2$, R$^3$, R$^4$, R$^5$ and R$^6$ must be a radical of formula Y-CR$^9$R$^{10}$-COOR$^{11}$ wherein Y, R$^9$, R$^{10}$ and R$^{11}$ are as defined in each instance herein; and with the additional proviso that when R$^1$ and/or R$^4$ is a radical of formula Y-CR$^9$R$^{10}$-COOR$^{11}$ wherein Y is NR$^{12}$ wherein R$^{12}$ is as defined herein, R$^9$ and R$^{10}$ together are oxo and R$^{11}$ is as defined herein, then at least one of R$^2$, R$^3$, R$^5$ and R$^6$ must be a radical of formula Y-CR$^9$R$^{10}$-COOR$^{11}$ wherein Y, R$^9$, R$^{10}$ and R$^{11}$ are as defined in each instance herein; or a therapeutically acceptable salt thereof.

2. A compound of formula I

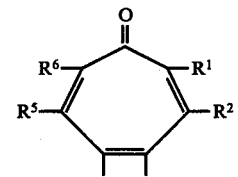

in which R$^1$, R$^2$, R$^3$, R$^4$, R$^5$ and R$^6$ are the same or different selected from the group consisting of hydrogen or a radical of formula Y-CR$^9$R$^{10}$-COOR$^{11}$ wherein Y is NR$^{12}$ wherein R$^{12}$ is hydrogen or lower alkyl, R$^9$ and R$^{10}$ together are oxo and R$^{11}$ is hydrogen or lower alkyl, with the proviso that one, two or three of R$^1$, R$^2$, R$^3$, R$^4$, R$^5$ and R$^6$ must be a radical of formula Y-CR$^9$R$^{10}$-COOR$^{11}$ wherein Y, R$^9$, R$^{10}$ and R$^{11}$ are as defined in each instance herein; and with the additional proviso that when R$^1$ and/or R$^4$ is a radical of formula Y-CR$^9$R$^{10}$-COOR$^{11}$ wherein Y is NR$^{12}$ wherein R$^{12}$ is as defined herein, R$^9$ and R$^{10}$ together are oxo and R$^{11}$ is as defined herein, then at least one of R$^2$, R$^3$, R$^5$ and R$^6$ must be a radical of formula Y-CR$^9$R$^{10}$-COOR$^{11}$ wherein Y, R$^9$, R$^{10}$ and R$^{11}$ are as defined in each instance herein; or a therapeutically acceptable salt thereof.

3. A compound of formula I

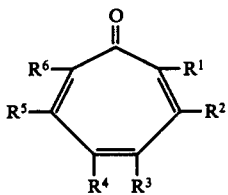

(1)

in which each of $R^1$ and $R^6$ is a radical of formula $Y$-$CR^9R^{10}$-$COOR^{11}$ wherein $Y$ is $NR^{12}$ wherein $R^{12}$ is hydrogen or lower alkyl, $R^9$ and $R^{10}$ together are oxo and $R^{11}$ is hydrogen or lower alkyl and $R^2$, $R^3$, $R^4$ and $R^5$ are hydrogen; or a therapeutically acceptable salt thereof.

4. [[3-[N-(2-Ethoxy-1,2-dioxoethyl)-N-methylamino]-2-oxo-3,5,7-cycloheptatrien-1-yl]amino]oxo-acetic acid ethyl ester, as claimed in claim 1.

5. A method for suppressing allergic manifestations of anaphylactic reactions and atopic hypersensitivity in a mammal which comprises administering to said mammal an effective amount of a compound of claim 1, or therapeutically acceptable salt thereof.

6. A pharmaceutical composition useful in suppressing allergic manifestations of anaphylactic reactions and atopic hypersensitivity comprising a compound of claim 1, or a therapeutically acceptable salt thereof, and a pharmaceutically acceptable carrier.

* * * * *